US006190859B1

(12) United States Patent
Putnak et al.

(10) Patent No.: US 6,190,859 B1
(45) Date of Patent: *Feb. 20, 2001

(54) METHOD AND KIT FOR DETECTION OF DENGUE VIRUS

(75) Inventors: J. Robert Putnak, Silver Spring; Kenneth Eckels, Rockville; Doria R. Dubois, Wheaton, all of MD (US); Kevin Cassidy, Toronto (CA)

(73) Assignee: The United States of America as represented by the Secretary of the Army, Washington, DC (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/422,458

(22) Filed: Apr. 17, 1995

(51) Int. Cl.[7] .................. A61K 39/12; C07K 14/18; C12N 7/04
(52) U.S. Cl. .................. 435/5; 435/7.1; 435/235.1; 435/236; 435/239; 424/218.1; 424/202.1; 424/184.1; 536/23.72; 530/300; 530/350; 530/388.3; 530/389.4
(58) Field of Search .................. 435/5, 7.1, 235.1, 435/236, 239; 424/218.1, 202.1, 184.1; 536/23.72; 530/300, 350, 388.3, 389.4

(56) References Cited

U.S. PATENT DOCUMENTS 4,164,566   8/1979   Provost et al. .................. 424/89
4,506,016   3/1985   Flehmig .................. 435/237

OTHER PUBLICATIONS

Eckels et al Dengue Virus Infections in Control of Virus Disease, second edition, Kurstak (ed) pp. 343–412, 1993.*
Feighny et al Am J Trop Med and Hyg vol. 47(4) 405–412, 1992.*
Mori et al. Trop. Med. Jun. 1986. vol. 28. No. 2 p. 87–99.*
Yamashita, T. et al. Japanese encephalitis purified vaccine II. Purity of the mouse brain vaccine purified by ultracentrifugation. Biken J. 13: 25–38, 1970.
Takaku, K. et al. Japanese encephalitis purified vaccine. Biken J. 11: 25–39, 1968.
Singh, B. et al. Semi–commercial–scale production of Japanese B encephalitis virus vaccines from tissue culture. App. Microbiol. 25: 945–951, 1973.
Dubois, D. R. Development of an inactivated dengue virus type 2 vaccine. Thesis dissertation, Catholic University. 1980.

* cited by examiner

*Primary Examiner*—Phuong T. Bui
(74) *Attorney, Agent, or Firm*—Elizabeth Arwine; Charles H. Harris; John Francis Moran

(57) ABSTRACT

An inactivated dengue virus vaccine to immunize and protect humans against dengue fever is described. The vaccine is based on dengue viruses which have been propagated to high titers in suitable cells, purified and inactivated under conditions which destroy infectivity but preserve immunogenicity, a high level of which is demonstrated in animal models. Uses of the inactivated dengue virus for detecting antibodies to dengue and kits therefor are also described.

8 Claims, 4 Drawing Sheets

Figure 2:
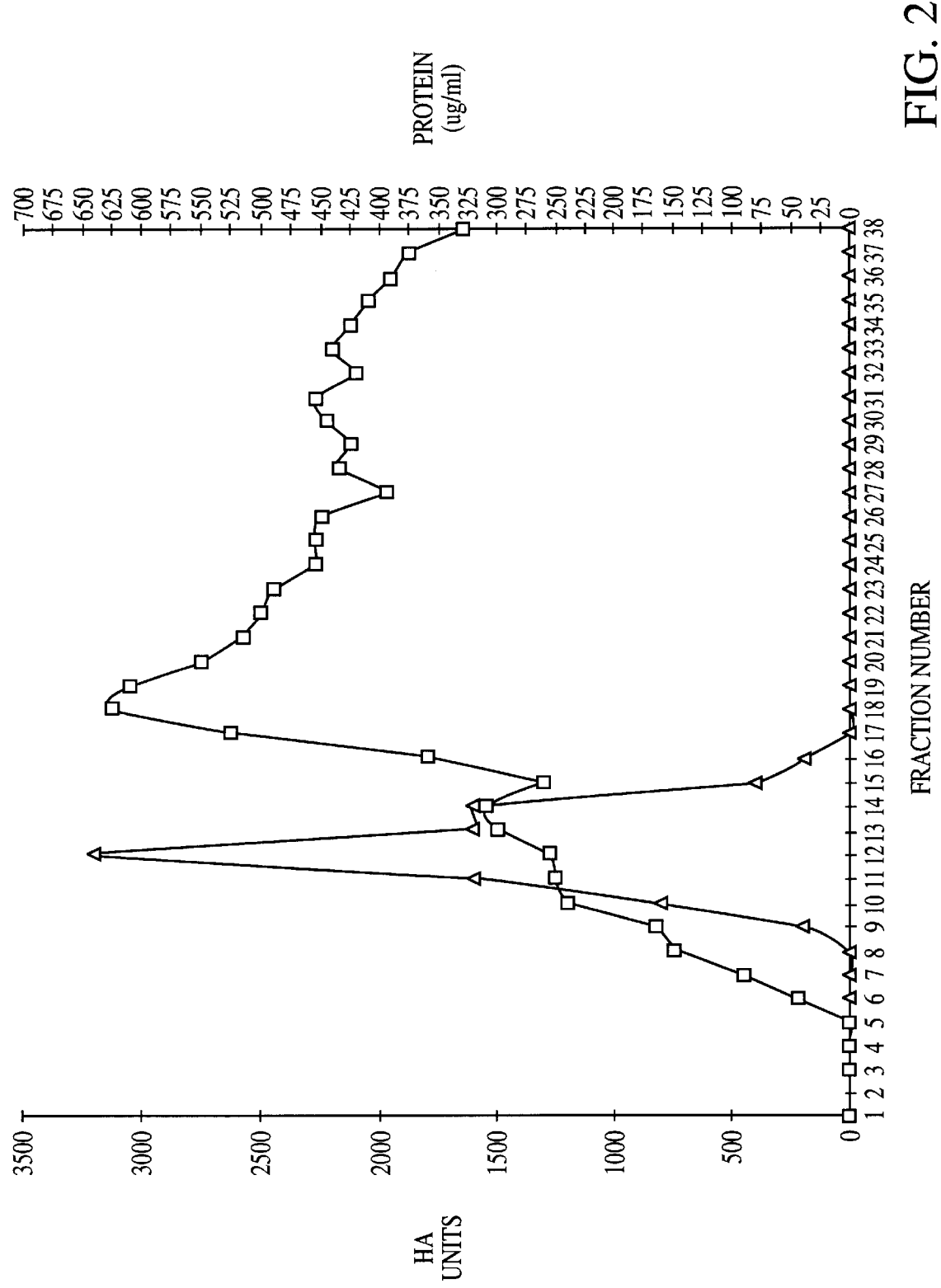
Figure 4:
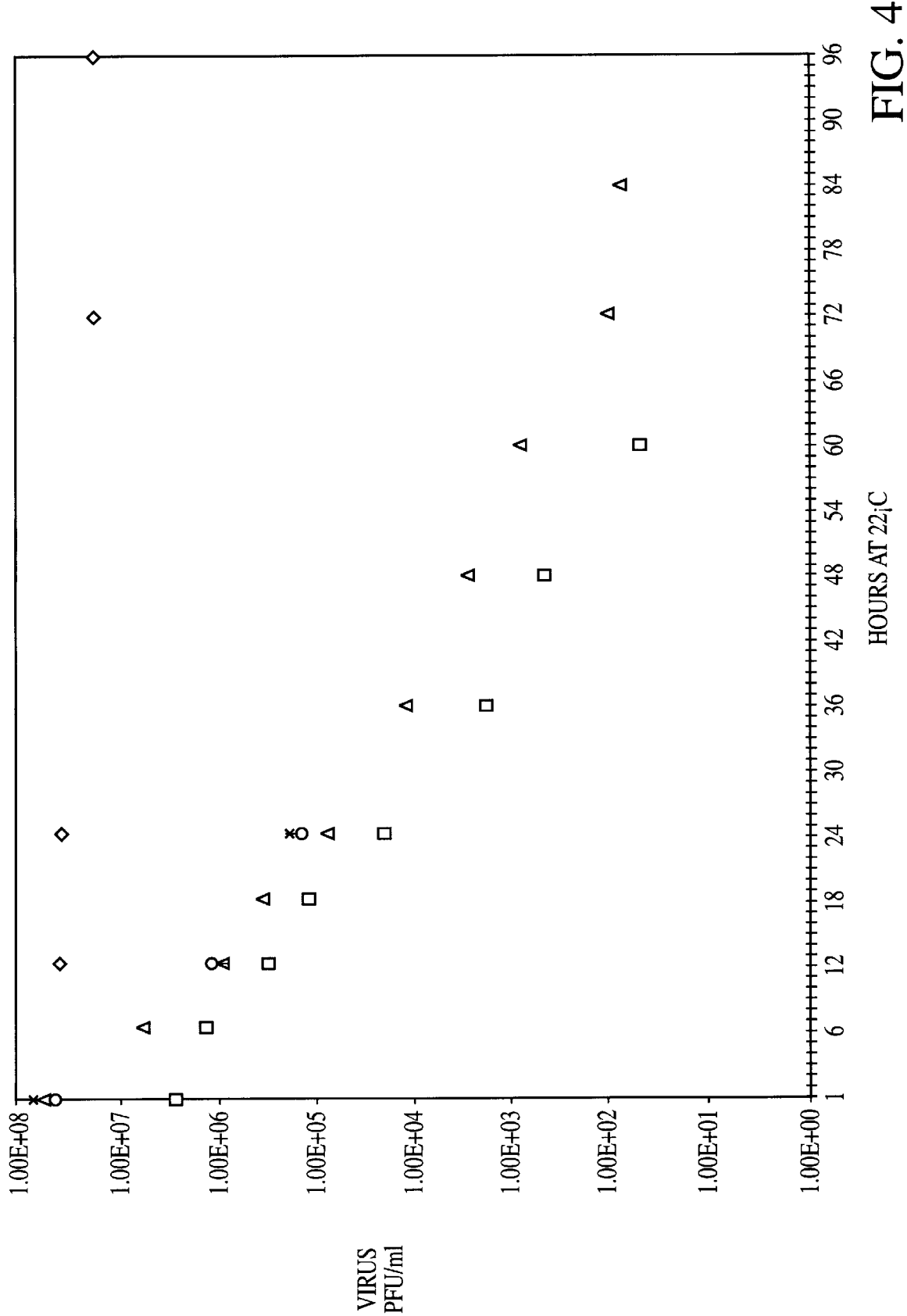

```
DENGUE-2 S16803 VIRUS              DENGUE-2 S16681 VIRUS
          │                                   │
          ▼                                   ▼
  ADAPT TO VERO-PM CELLS             ADAPT TO FRhL-2 CELLS
          │                                   │
          ▼                                   ▼
  INFECT ROLLER CULTURES             INFECT ROLLER CULTURES
          │                                   │
          ▼                                   ▼
 REFEED W/ OR W/O 0.25% HSA            REFEED W/ 2% FBS
          │                                   │
          ▼                                   ▼
   HARVEST SUPES ONCE                  HARVEST SUPES DAILY
      @ 5 DAYS PI                         @ 4-7 DAYS PI
          │                                   │
          ▼                                   ▼
     CONCENTRATATE BY                 CONCENTRATE BY PEG Ppte.
      ULTRAFILTRATION                  AND ULTRACENTRIFUGATION
          │                                   │
          ▼                                   ▼
     PURIFY ON SUCROSE                   PURIFY ON SUCROSE
         GRADIENTS                           GRADIENTS
          │                                   │
          ▼                                   ▼
    POOL HA (+) FRACTIONS              POOL Ag (+) FRACTIONS
          │                                   │
          ▼                                   ▼
    DILUTE IN M199 OR PBS             PELLET VIRUS; RESUSPEND
                                             IN M199
          │                                   │
          ▼                                   ▼
       FILTER (0.22UM)                    FILTER (0.22UM)
                   \                      /
                    \                    /
                     ▼                  ▼
                  INACTIVATE W/ 0.05%
                       FORMALIN OR
                    60CO IRRADIATION
```

FIG. 1

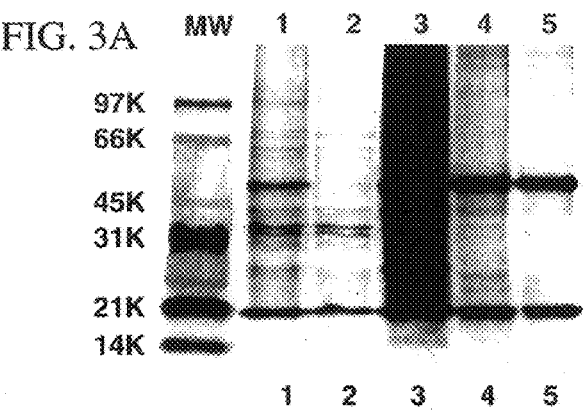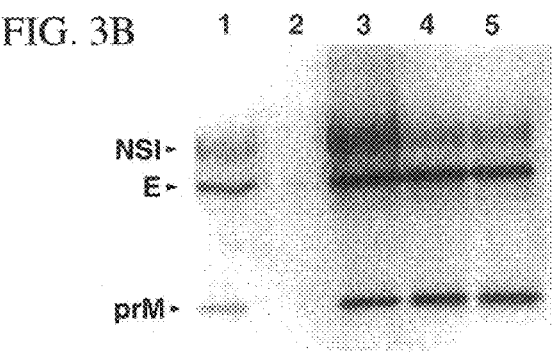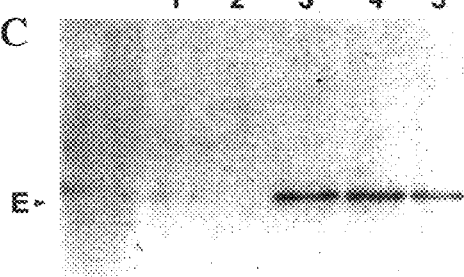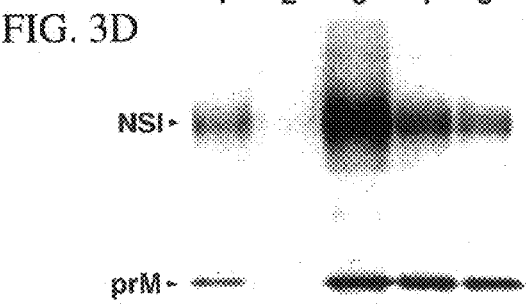

METHOD AND KIT FOR DETECTION OF DENGUE VIRUS

INTRODUCTION

Dengue is an acute viral disease of man which is transmitted by mosquitos. It is endemic in the tropics and subtropics, worldwide, where an estimated 100,000,000 cases occur annually (Reviewed in Henchal and Putnak, *Clin. Microbiol. Revs* 3: 376–96, 1990. The entire content of all documents cited herein are hereby incorporated by reference). Dengue is characterized clinically by biphasic fever, rash and hematopoietic depression, and by constitutional symptoms such as malaise, arthralgia, myalgia and headache (Reviewed in Monath, Flaviviruses. In: Fields, B. N. et al. *Fields Virology,* 2nd ed. Vol 1, New York: Raven Press, 1990, p. 763–814). Infrequently, more severe disease is seen, manifested by hemorrhage which may progress to lethal shock (Halstead, S. B. *Yale J. Biol. Med.* 37: 434–54, 1965). The timing of these manifestations, somewhat after the early febrile period, and their frequent association with secondary dengue infection and pre-existing antibody has led to the hypothesis that they are immunologically mediated (Halstead, S. B. *Yale J. Biol. Med.* 42: 350–62, 1970; Sankawibha et al. *Am. J. Epidemiol.* 120: 653–69, 1984). Although relatively rare, dengue hemorrhagic fever (DHF) and dengue shock syndrome (DSS) may be significant causes of death in children. At present, there is no vaccine to protect against dengue and attempts to prevent disease by controlling the mosquito vector have proven largely ineffective.

Dengue viruses are members of the family *flaviviradae* which includes over sixty members (Westaway, E. G. et al. *Intervirology* 24:183–92, 1985). Within the dengue group are four serotypes, dengue-type-one (dengue-1), dengue-2, dengue-3, and dengue-4, among which there is considerable genetic and antigenic similarity but no significant cross-neutralization (Calisher C. H. et al. *J. Gen. Virol.* 70: 37–43, 1989). Like the family prototype, yellow fever (YF) virus, they are enveloped, single-stranded RNA viruses approximately 50 nm in size (Reviewed in Henchal and Putnak, 1990, supra). Their 10.5 kilobase (kb) genome encodes ten proteins, three virion structural proteins at the 5' end of the RNA beginning with capsid (C), matrix (M), its precursor pre-matrix (prM) and envelope (E), followed by seven nonstructural (NS) proteins, NS1, NS2A, NS2B, NS3, NS4A, NS4B and NS5 (Chambers, T. J. et al. Annu. Rev. Microbiol. 44: 649–88, 1989). Virus neutralizing antibody, thought to play a primary role in immunity, is directed against the E protein (Qureshi, A. A. and Trent, D. W. *Infect. Immun.* 8: 993–9, 1973; Gentry, M. K. et al. *Am. J. Trop. Med. Hyg.* 31: 548–55, 1982), however, antibodies and T-cells directed against epitopes of other structural and even nonstructural proteins may also be important in subserving immunity to virus infection (Schlesinger, J. J. et al., *J. Gen. Virol.* 68:853–57, 1987).

Currently, only two flavivirus vaccines have been licensed by the United States Food and Drug Administration (FDA) for human use, live-attenuated yellow fever virus (17D strain) developed by Theiler and coworkers in the 1930s (Theiler, M. and Smith, H. H. *J. Exp. Med.* 65: 748–800, 1937), and purified, formalin-inactivated Japanese encephalitis (JE) virus developed in the 1960s in Japan (Takaku , K. et al., *Biken J. 11:25–39, 1968*). Both have proven to be safe and effective, eliciting high titers of virus-neutralizing antibody and conferring solid protection (Hoke, C. H. et al. *N. Engl. J. Med.* 319: 608–13, 1988; Reviewed in Monath, 1990, supra). Also of note is a purified, formalin-inactivated vaccine for tick-borne encephalitis virus developed in the 1970s in Austria (Kunz, C. et al. *J. Med. Virol.* 6: 103–9, 1980) which is used successfully in many European countries.

In recent attempts to develop second generation flavivirus vaccines, much work has been done using recombinant, complimentary DNA (cDNA) technology (Reviewed in Schlesinger, J. J. et al. In: Ellis R. W. *Vaccines: New Approaches to Immunological Problems.* Boston: Butterworth-Heinemann, 1992, p. 289–307; and Putnak, R. In: Kurstak E. *Modem Vaccinology.* New York: Plenum Medical, 11: 231–52, 1994). Full-length, infectious, cDNA clones which are now available for YF (Rice, C. M. et al. *New Biologist* 1: 285–96, 1989), JE (Sumiyoshi, H. et al. *J. Virol.* 66: 5425–31, 1992), and dengue-4 (Lai, C. J. et al. *Proc. Natl. Acad. Sci. U.S.A.* 88: 5139–43, 1991) viruses offer the exciting possibility of making genetically-engineered attenuated vaccines, while in vitro expression systems allow production of recombinant subunit antigens (Reviewed in Putnak, 1994, supra). Although promising, these technologies have yet to yield practical alternatives to existing vaccines.

The history of dengue virus vaccine development goes back more than fifty years, beginning with attempts in the 1920s to inactivate dengue viruses from infectious human plasma with ox bile or formalin (Simmons, J. S. et al. In: Brown W. H. *Monographs of the Bureau of Science, Monograph 29.* The philippines: Manila Bureau of Printing 1:489, 1931), and attempts in the 1940s to attenuate viruses by serial passage in the brains of suckling mice (Sabin, A. B. and Schlesinger, R. W. *Science* 101: 640–42, 1945). More recent attempts to make attenuated dengue vaccines by serial passage of viruses in primary cell cultures have met with some success (Eckels, K. H. et al. *Infect. Immun.* 27: 175–80, 1980, Am. J. Trop. Med. Hyg. 33: 684–89, 1984; Halstead, S. B. et al. *Am J. Trop. Med. Hyg.* 33: 679–83, 1984; Bancroft, W. H. et al. *J. Infect. Dis.* 149: 1005–10, 1984; Bhamarapravati, N. et al. WHO Bull. 65: 189–95, 1987; Bhamarapravati, N. and Yoksan, S. *Lancet* 8646: 1077, 1989; Hoke, C. H. Jr. et al. *Am. J. Trop. Med. Hyg.* 43: 219–26, 1990; Reviewed in Brandt, W. et al. *Am J. Trop. Med. Hyg.* 16: 339–47, 1967; Edelman, R. et al. *J. Infect. Dis.* 170: 1448–55, 1994), although it has been difficult to identify candidates which are both suitably attenuated and immunogenic, nor is it certain that these viruses will prove to be genetically stable.

Despite the existence of several safe, effective, and economical inactivated viral vaccines, it has been contended that such an approach is neither feasible nor practical for dengue because of the relatively poor growth of these viruses in culture and their questionable antigenic stability after purification. A dengue virus vaccine candidate has been produced previously using unpurified, formalin-inactivated type 2 viurs (Dubois, D. R., Ph.D. Thesis, The Catholic University of America, 1980). However, this preparation did not elicit high titers of anti-dengue virus antibody nor did it uniformly protect mice, an accepted animal model, against virus challenge. In addition, this study did not demonstrate that dengue viruses could be propagated to high titers or employ purified viruses in making the vaccine, thus, the vaccine described in this study was not likely to be practical or suitable for use in humans.

Therefore, in view of the above, there is a need for a dengue virus vaccine which will elicit high titers of virus neutralizing antibody, protect against viral infection without risk of disease to the immunized mammal, is physically stable allowing easy and economical transport and storage, and is suitable for human use.

SUMMARY

The present invention is directed to a vaccine that satisfies this need. The purified inactivated dengue viruses vaccine of the present invention has a major advantage over attenuated dengue virus in that inactivated viruses are not infectious and therefore, can not revert to virulence or cause disease. Another advantage of inactivated over attenuated dengue viruses is their potentially greater physical stability (e.g., to temperature changes) allowing easy and economical transport and storage of the vaccine. In addition, inactivated dengue viruses may be expected to afford enhanced immunogenicity and greater protection against disease than recombinant dengue proteins due to their native conformation.

The purified, inactivated dengue virus vaccine of the present invention is based on dengue viruses which have been propagated to high titers in cell lines suitable for making human-use products. These viruses are obtained by screening from among several wild virus isolates of known passage history for those strains which replicate to the highest titers in cells certified free of pathogens. Since there are four serotypes of dengue virus which may cause disease, i. e., dengue-type-one (dengue-1), dengue-2, dengue-3, and dengue-4, and no cross-neutralization or cross-protection exists among serotypes, one representative of each serotype is selected for inclusion into the final vaccine in order to guarantee protection against disease from any of the four serotypes.

By “viruses” is meant different serotypes of viruses causing the same disease or different strains of viruses responsible for different diseases. Since this invention describes the production of a vaccine using viruses from different serotypes, it is understood that the present invention also encompasses vaccines which combine different strains of viruses.

These candidate vaccine viruses from the four serotypes of dengue viruses are then further adapted by additional cell culture passages to make high-titered master (first passage) and production (second passage) seed lots. The viruses are then purified from cell culture supernates and treated with an appropriate chemical agent such as formalin which preserves their antigenicity and immunogenicity while destroying their infectivity. The inactivated virus is mixed with a suitable adjuvant and used to immunize mammals in order to elicit high titers of virus neutralizing antibodies and protect the immunized mammal from disease caused by dengue virus.

The inactivated dengue virus(es) can also be used as a dengue diagnostic antigen to detect dengue antibodies in exposed individuals. Inactivated virus can replace live dengue virus which is currently used in diagnostic assays, thus eliminating the risk of infection to the test operator. The present invention is also superior to recombinant antigens as diagnostic reagents because of the potentially greater antigenic fidelity of inactivated virus.

Therefore, it is an object of the present invention to provide a vaccine comprising purified, inactivated dengue virus(es) for immunizing mammals and providing protection against disease.

It is another object of the present invention to provide a method for producing purified, inactivated dengue virus(es) for use in a vaccine.

It is still another object of the present invention to provide a safe diagnostic assay for the detection of dengue virus infection or anti-virus antibodies in serum or tissue of an individual suspected of having the disease.

DRAWINGS

These and other features, aspects, and advantages of the present invention will become better understood with regard to the following description, appended claims, and accompanying drawings as follows:

FIG. 1. Production scheme for inactivated dengue-2 pilot vaccines. Shows an overview of the processes used to produce several lots of purified, inactivated dengue-2 viruses.

FIG. 2. Purification of dengue-2 virus by sucrose gradient ultracentrifugation. Twenty-three ml of concentrated culture supernate was applied to a fifteen ml 15–60% sucrose gradient and centrifuged in an SW 28 rotor at 17,000 rpm, 18 hrs., 4 C. One ml samples were collected from the bottom of the tube and assayed for virus hemagglutinin (triangles) and total protein (boxes). Data shown are from dengue-2, S16803 virus, lot WR4.

FIG. 3. Analysis of dengue-2 virus by SDS-PAGE and Western blotting. Samples obtained during purification of dengue-2, S16803, virus (lot WR 4) were subjected to SDS-PAGE and the resolved proteins transferred to IMMOBILON-P™ membranes, a nitrocellulose membrane membranes. Proteins were visualized by staining with colloidal gold (FIG. 3A), and antigens were visualized by reaction with anti-dengue-2 polyclonal HMAF (FIG. 3B), monoclonal antibodies 2H3, 3H5 and 4E9 reactive against E antigen (FIG. 3C), and monoclonal antibodies 14E9 and 7E11 reactive against prM/M and NS1 antigens (FIG. 3D). Lane 1, cell culture supernate; lane 2, filtrate (flow-through) after ultrafiltration; lane 3, concentrate (retentate) after ultrafiltration; lane 4, sucrose gradient pool; lane 5, filtered sucrose gradient pool. Molecular weight markers are in left-hand 2 lanes.

FIG. 4. Formalin inactivation kinetics of purified dengue-2 viruses. Purified dengue-2, S16803, virus preparations were inactivated with 0.05% formalin at 22 C. Samples taken at the indicated times were titrated for infectious virus by plaquing on LLC-MK2 cell monolayers. Inactivation time points from four separate experiments are shown: WR 1 (boxes), WR 2 (Triangles), WR 3 (Circles), and WR 4 (x’s). Thermal inactivation (no formalin) control (filled diamonds) was done in parallel with WR 2.

DESCRIPTION

In one embodiment the present invention relates to a method for the production of high titers of dengue virus, said method comprising: (i) screening from several strains of dengue virus representing each of the four serotypes for those viruses which grow to the highest titers, for example from $5\times10^6$ to $5\times10^7$ pfu/ml, preferrably at least $1\times10^7$ pfu/ml in the cell line(s) of choice; (ii) selecting those strains of dengue virus which grow to the highest titers in the cell line(s) of choice; and (iii) further adapting those selected strains for enhanced growth by additional passage from one to several times in the cell line(s) of choice.

In another embodiment, the present invention provides a method for purifying virus from cell culture without freezing the crude or interim purity materials. Said method comprising the steps of: (i) removing cell debris; (ii) concentrating the virus; (iii) purifying the virus; and (iv) fractionating the gradients and assaying the fractions for virus. More specifically, the present invention provides a method for the production of purified dengue virus(es) by propagating viruses to high titer in primary or continuous cell lines, in the presence or absence of serum protein supplements, purifying the viruses by ultracentrifugation, and pooling the virus-positive fractions.

In still another embodiment, the present invention provides for a method of inactivating dengue virus(es) to destroy their infectivity while preserving their antigenicity and immunogenicity. Said method comprising adding an effective quantity of an agent, such as formalin or β-propriolactone, which would inactivate the virus while retaining its antigenicity, and incubating said virus with said agent such that said virus is inactivated. Alternatively, inactivation can be achieved by irradiating said virus with a radioactive source until said virus is inactivated, said radioactive source being for example cobalt-60, at doses sufficient to inactivate the infectivity of the viruses while preserving the antigenicity essentially intact. Examples of useful doses are those which fall within the range from 5.5 to 7.0 Mrads.

In yet another embodiment, the present invention relates to a method for the production of a purified, inactivated virus(es) vaccine, specifically, a method for producing a purified inactivated dengue virus(es) vaccine. Said method comprising the steps of: propagating virus(es) to high titer in cells, harvesting said virus(es) from cell culture supernatants, concentrating said virus(es), purifying said virus(es) as discussed above, inactivating said virus(es) as discussed above, and optionally, mixing said purified, inactivated virus(es) with suitable reagent for administration to mammals by known methods in the art. Cells producing high titers of dengue virus include continuous cell lines commonly available, for example, Vero cells (Vero-PM strain), CV-1 cells, LLC-MK2 cells, primary cell lines such as fetal Rhesus lung (FRhL-2) cells, BSC-1 cells, and MRC-5 cells, or human diploid fibroblasts. It is essential that cells used for virus growth be free from adventitious agents and, in addition, said cells must be demonstrated safe and non-tumorigenic in animal safety tests. It is also desirable that the chosen cell(s) be able to maintain dengue virus replication at high titers in the absence of supplementary serum proteins, as such additives may result in virus of a lesser purity.

Harvesting viruses from cell culture can be accomplished by common methods known in the art including slow-speed centrifugation (for example at 1500×g for 10 min), or by filtration through a filter of pore size of 0.45 μm;. Methods for concentrating said virus(es) are within the scope of a person with ordinary skill in the art and include, for example, ultrafiltration (the membrane should be no greater than 300 kDa pore size), or precipitation with PEG 8000. Methods for purifying said viruses are known to a person with ordinary skill in the art and include continuous or multi-step sucrose gradients, purification by column chromatography using size exclusion, ion exchange, adsorption, or affinity columns, or purification by partitioning in polymer two-phase or multi-phase systems, and any combination thereof. Methods for assaying for virus positive fractions include plaque assay, hemagglutination (HA) assay, and/or antigen assays such as immunoassays.

Typically, vaccines are prepared as injectables, either as liquid solutions or suspensions; solid form suitable for solution in, or suspension in, liquid prior to injection may also be prepared. The preparation may also be emulsified, or the ingredients are often mixed with excipients which are pharmaceutically acceptable and compatible with the inactive virus(es). Suitable excipients are, for example, saline or buffered saline (pH 7 to 8), or other physiologic, isotonic solutions which may also contain dextrose, glycerol or the like and combinations thereof. However, agents which disrupt or dissolve lipid membranes such as strong detergents, alcohols, and other organic solvents should be avoided. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-Lthreonyl-D-isoglutamine (thr-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and TIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the virus resulting from administration of the inactive virus in vaccines which are also comprised of the various adjuvants.

In yet another embodiment, the present invention relates to a purified, inactivated virus(es) vaccine, specifically, purified, inactivated dengue virus vaccine. The vaccine may be prepared in the form of a mixed vaccine which contains one strain or several different strains of inactivated virus(es) prepared as described above. Further, the vaccine can include at least one other antigen as long as the added antigen does not interfere with the effectiveness of the purified, inactivated virus(es) vaccine and the side effects and adverse reactions are not increased additively or synergistically.

The vaccine can be administered in the form of a liquid or suspension prepared as discussed above. Additional formulations which are suitable for other modes of administration include suppositories and, in some cases, oral formulations. Additionally, the vaccine can be lyophilized. For suppositories, traditional binders and carriers may include, for example, polyalkylene glycols or triglycerides; such suppositories may be formed from mixtures containing the inactive virus generally in a range of 0.1–100 μg. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations, nose drops or powders and contain 10–95% inactive virus.

Generally, the vaccine may be administered subcutaneously, intradermally, or intramuscularly in a dose effective for the production of neutralizing antibody and protection. The vaccines are administered in a manner compatible with the dosage formulation, and in such amount as will be prophylactically and/or therapeutically effective. The quantity to be administered, which is generally in the range of 0.1–100 μg of inactivated virus per dose, depends on the subject to be treated, capacity of the subject's immune system to synthesize antibodies, and the degree of protection desired. Precise amounts of the vaccine to be administered may depend on the judgement of the practitioner and may be peculiar to each subject.

The vaccine may be given in a single dose schedule, or preferably a multiple dose schedule in which a primary course of vaccination may be with 1–10 separate doses, followed by other doses given at subsequent time intervals required to maintain and or reinforce the immune response, for example, at 1–4 months for a second dose, and if needed, a subsequent dose(s) after several months. The dosage regimen will also, at least in part, be determined by the need of the individual and be dependent upon the judgment of the practitioner. Examples of suitable immunization schedules include: (i) 0, 1 month and 6 months, (ii) 0, 7 days and 1 month, (iii) 0 and 1 month, (iv) 0 and 6 months, or other schedules sufficient to elicit titers of virus-neutralizing antibodies expected to confer protective immunity (e.g. final titers >80 as measured in a virus plaque reduction neutralization assay). The generation of protective immunity against dengue with an inactivated virus vaccine may reasonably be expected after a primay course of immunization consisting of 1 to 3 inoculations. These could be supplemented by boosters at intervals (e.g., every two years) designed to maintain a satisfactory level of protective immunity.

In a further embodiment, the present invention relates to a method of detecting the presence of viral antigens or antibodies against a virus, in particular, dengue virus, in a sample. Protocols may be based, for example upon competition, or direct reaction, or sandwich type assays. Protocols may also, for example use solid supports, or may be by immunoprecipitation. Most assays involve the use of a label; the labels may be, for example, fluorescent, chemiluminescent, radioactive, or dye molecules. Assays which amplify the signals from the probe are also known: examples of which are assays which utilize biotin and avidin, and enzyme-labeled and mediated immunoassays, such as ELISA assays. Using standard methodology well known in the art, a diagnostic assay can be constructed, for example, by coating a surface (i.e. a solid support) for example, a microtitration plate or a membrane (e.g. nitrocellulose membrane), with said inactivated virus described above, and contacting it with the serum of a person suspected of having a viral infection. The presence of a resulting complex formed between the inactivated virus and antibodies specific therefor in the serum can be detected by any of the known methods common in the art, such as fluorescent antibody spectroscopy or colorimetry. This method of detection can be used, for example, for the diagnosis of flavivirus infection.

In still another embodiment, the present invention relates to a diagnostic kit which contains the purified, inactivated virus(es) and ancillary reagents that are well known in the art and that are suitable for use in detecting the presence of antibodies to said virus(es) in serum or tissue sample. Tissue samples contemplated can be monkey and human, or other mammals. The appropriate reagents and materials required for the conduct of the assay can be packaged along with a suitable set of assay instructions.

Described below are examples of the present invention which are provided only for illustrative purposes, and not to limit the scope of the present invention. In light of the present disclosure, numerous embodiments within the scope of the claims will be apparent to those of ordinary skill in the art.

The following MATERIALS AND METHODS were used in the examples that follow.

Cells. Cells used for virus production were African Green Monkey kidney cells, certified free from adventitious agents (Vero-PM line) which were a gift from Pasteur-Merieux, Paris, France, and primary fetal rhesus monkey lung DBS-FRhL-2 (FRhL-2) cells. For plaque titration of viruses, LLC-MK2 cells or the Hawaii line of Vero cells (H-Vero) were used (see below). For amplification of viruses, Singh's clone of *Aedes albopictus* cells (C6/36) were used (see below).

Viruses. An isolate of Dengue-2 virus (strain 16681) which had been passaged 40 times in primary dog kidney cells (PDK-40) was passaged 4 additional times in FRhL-2 cells; a master seed was made at FRhL-2 cell passage level 5, a production seed at passage 6, and vaccine lots at passage 7. Dengue-2 virus (strain S16803) which had been passaged 1 time in C6/36 cells was passaged 3 additional times in Vero-PM cells to make pre-master, master, and production seeds. Vaccine lots were made at Vero-PM cell passage level 4.

Antibodies. Mouse hyperimmune ascitic fluid (MHAF) reactive against all structural and nonstructural antigens of dengue-2 virus was prepared as previously described (Brandt, W. E. et al., 1967, supra). Mouse ascitic fluids containing monoclonal antibodies specific for E antigen (2H3, 3H5 and 4E5), prM/M antigen (14E9) and NS 1 antigen (7E 1) have previously been described (Gentry, M. K. et al., 1982, supra; Henchal, E. A. et al. *Am. J. Trop. Med. Hyg.* 32: 164–200, 1983, *Am. J. Trop. Med. Hyg.* 43: 219–26, 1985).

Virus production in Vero-PM cell culture. Vero-PM cells (passage 139) stored in liquid $N_2$ were thawed rapidly at 35 C. One ml of cell suspension was used for each 150 $cm^2$ (T150) flask (Coming). Cells were fed with 50 ml of growth medium (GM): Eagle's minimum essential medium (EMEM, Whittaker), 10% heat-inactivated (56 C, 30 min) fetal bovine serum (FBS, Whittaker), 2 mM L-glutamine (Whittaker), 100 units of streptomycin and neomycin (S/N), and incubated at 35 C. Upon confluency, cells were trypsinized and one T150 flask was sub-cultured into each 490 $cm^2$ roller bottle (Corning). Roller cultures were fed with 100 ml GM and incubated at 35 C on a roller apparatus set to rotate at a rate of 0.5 rpm. Under these conditions Vero cells formed monolayers which were 90–100% confluent within 5 days. Monolayers were infected at a multiplicity of infection (MOI) of 0.01 plaque-forming units (PFU) per cell. Virus was allowed to adsorb for 1 hr at 35 C, then cells were refed with 100 ml of maintenance medium (MM, i.e., same as GM except containing 0.25% human serum albumin, HSA) and incubated at 35 C. In some experiments cells were washed with serum-free EMEM at two days post-infection (PI) and then refed with serum-free medium. Culture supernates were pooled for virus harvest at five days PI when CPE was about 75%.

Virus production in FRhL-2 cell culture. FRhL-2 cells (passage 30) were grown at 35 C in 175 $cm^2$ flasks (Falcon) with growth medium consisting of EMEM, 10% heat-inactivated FBS, 2 mM L-glutamine, 1% of 100× non-essential aminoacids and 1% of 100× penicillin and streptomycin. Upon confluency, cells were trypsinized and subcultured using a split ratio of 1:2 based on surface area into either 1585 $cm^2$ borosilicate glass roller bottles or 1750 $cm^2$ plastic roller bottles (Corning). Cultures were fed with 145 ml of growth medium and incubated at 35 C on a roller apparatus set to rotate at 0.5 rpm. Under these conditions monolayers reached 90–95% maximum confluency in seven days. Monolayers were infected at a MOI of 0.02 PFU/cell, and after virus adsorption, refed with medium containing 2% heat-inactivated FBS. Infected cultures were incubated at 32 C. The culture media was changed daily beginning at 2 days PI and culture supemates were harvested daily beginning at 4 days PI and refrigerated prior to pooling and processing or, alternatively, concentrated by PEG precipitation before pooling and further processing.

Virus concentration by polyethylene glycol (PEG) precipitation. Supernate fluids from infected FRhL-2 cell cultures were clarified by centrifugation (J6-B centrifuge, Beckman) at 2,300 rpm (1,500×g) for 10 min. The clarified supernate was adjusted to 6% PEG 8000 (Sigma) and 0.5 M NaCl and held at 4 C with gentle stirring for 45 min. The precipitate was collected by centrifugation at 4,200 rpm (5000×g) for 50 min and resuspended in STE buffer (0.1 M NaCl, 10 mM tris, 1 mM EDTA, pH 7.6) for a concentration of 10–30 fold. The virus suspension was then clarified by centrifugation (J2-20 centrifuge, Beckman) in a JA-18 rotor at 10,500 RPM (12,000×g) for 10 min at 4 C. The pellet was discarded. The supernate was then centrifuged in a Beckman type 55.2 Ti rotor at 46,000 RPM (170,000×g) for 80 min at 4 C to pellet virus. The virus pellet was resuspended in STE buffer in a volume which resulted in a further 13-fold concentration.

Virus concentration by tangential flow ultrafiltration. Supernate fluids from infected Vero-PM cell cultures were clarified by centrifugation at 1,500 rpm for 10 min in a Sorval RT 6000 B centrifuge and then filtered through a 0.45 um CN filter (Nalgene). The filtered supernate was concentrated by tangential flow ultrafiltration using a low-protein-binding 100 kda-cutoff membrane (omega 100K screen channel, Filtron, Inc.). Concentration was carried out at 4 C using a flow rate of 400 ml per min, a filtration rate of approximately 100 ml per min and a pressure of 20–30 psi. The processing time for a fifteen to twenty-fold reduction in volume was approximately 10 min. Following concentration, samples were held briefly at 4 C prior to sucrose gradient ultracentrifugation.

Sucrose gradient ultracentrifugation. Virus was purified on sucrose gradients essentially as described previously (Srivastava, A. K. et al. Arch. Virol. 96: 97–107, 1987) with minor modifications. Fifteen ml sucrose gradients were made in 141 ×3.5" (40 ml) ultracentifuge tubes (Ultraclear™, Beckman, Inc.) by stepwise addition of the following w/w sucrose solutions in phosphate buffered saline, pH 7.4 (PBS, without Ca and Mg, Whittaker MA Bioproducts): 2 ml 60%, 2 ml 55%, 2 ml 50%, 2 ml 45%, 2 ml 40%, 2 ml 35%, 2 ml 30% and 1 ml 15%. A smooth gradient was formed by allowing the tubes to stand for 24 hrs at room temperature. Up to 25 ml of concentrated virus was applied to each tube. Ultracentrifugation was carried out in a SW 28 rotor (Beckman) at 17,000 rpm for 18 hrs at 4 C. Following centrifugation, 1 to 2 ml fractions were collected from the bottom of the tubes. Fractions were assayed for total protein, virus HA, and virus antigen (see below). For virus grown in Vero-PM cells, gradient fractions positive by the HA test (see below) were pooled and diluted to 10% or less sucrose with Medium 199 (M199, Gibco-BRL) or PBS. For virus grown in FRhL-2 cells, the antigen-positive peak fractions, determined by spot blot assay (see below), were pooled, the virus was pelleted by centrifugation in a Beckman 55.2 Ti rotor at 46,000 rpm for 80 min at 4 C, and then resuspended in M199. Prior to formalin inactivation, virus pools were filtered through a 0.22 um low-protein-binding filter (GV type, Millipore).

Virus inactivation with formalin. Formalin (37% formaldehyde, ACS grade, Fisher) was diluted 1:40 in PBS, the pH was adjusted to 7.4 with 1 N NaOH and the solution was sterilized by passage through a 0.22 um CN filter (Nalgene). One volume of this solution was added to 50 volumes of purified virus for a final formalin concentration of 0.05%. Inactivation was carried out in a sterile polypropylene tube (Coming) at 22 C in a constant temperature water bath. After 48 hrs, virus was filtered through a 0.22 um GV type filter and transferred to a fresh container. Aliquots were taken at regular intervals to measure infectious virus and virus antigen. Free formalin in the samples was neutralized by the addition of one volume of a 1:8 dilution of a 35% (w/v) aqueous solution of sodium bisulfite to 100 volumes of sample. For plaque assay, one-half of each sample was transferred to a tube containing an equal volume of heat-inactivated FBS and frozen at −80 C. At the completion of inactivation, free formalin in the bulk culture was neutralized by addition of an equimolar amount of sterile 10% w/v sodium bisulfite.

Virus inactivation with gamma irradiation. Virus aliquots of 50 uL in 1.5 ml sterile polypropylene tubes were frozen and placed on dry ice in the gamma cell of a $^{60}$Co source (Laboratory Centers for Disease Control, Ottawa, Canada). Doses delivered to the virus samples ranged from 0 to 7 MRads at a dose rate of 0.63 MRads/hr (6.3 kGy/hr). Aliquots were retrieved at various intervals to measure infectious virus and virus antigen.

C6/36 cell virus amplification assay. C6/36 cells at passage level 15–30 were grown as monolayers in 25 cm$^2$ (T25) flasks with EMEM, nonessential amino acids (BioWhittaker), 10% heat-inactivated FBS and S/N, at 28 C. Upon confluency, the growth medium was removed and duplicate flasks were inoculated with samples from virus-inactivation timepoints. After a 1 hr adsorption period at 35 C, cells were refed and incubated at 28 C. Cells were refed after 7 days and at 14 days the culture media was harvested and plaqued to detect infectious virus (see below).

Virus plaque titration assay. Virus infectivity titrations were performed by plaqueing on LLC-MK2 cell (Sukhavachana, P. et al. WHO Bull. 35: 65–6, 1966) or H-Vero cell monolayers.

Virus plaque reduction neutralization (PRNT) assay. Anti-dengue-2 virus neutralizing antibody was measured in pooled sera from immunized mice using an assay (Russell, P. K. et al. J. Immunol. 99: 285–90, 1967) which was modified by inclusion of a heat-labile factor provided by normal (non-dengue-immune) human plasma in order to enhance antibody-dependant neutralization (Chappell, W. A. et al. Appl. Microbiol. 21: 79–83, 1971). The reciprocal of the serum dilution which gave a 50% reduction in the number of virus plaques (PRNT-50%) was taken as the endpoint.

Virus hemagglutination (HA) and hemagglutination-inhibition (HI) assays. Virus HA and HI assays were performed as previously described (Clarke, D. H. and Casals, J. Am. J. Trop. Med. Hyg. 7: 561–73, 1958).

Antigen spot blot assay. To detect and quantitate antigen in inactivated virus preparations, an antigen spot-blot assay was performed. Virus samples were diluted out serially two-fold and spotted onto nitrocellulose paper. The papers were air-dried, blocked with 5% casein in PBS, and incubated with anti-dengue-2 HMAF followed by enzyme-linked secondary antibody as previously described (Feighny, R. et al. Am. J. Trop. Med. Hyg. 47(4): 405–12, 1992).

Sodium dodecyl sulfate-polyacrylamide gel electrophoresis (SDS-PAGE) and Western blotting. Proteins were solubilized in SDS-PAGE sample buffer containing 1% SDS, 66 mM Tris-HCl, pH 6.8, 1% glycerol and 0.7% bromphenol blue at 22 C for 10 min and electrophoresed on 12.5% polyacrylamide gels (Feighny, R. et al. Am. J. Trop. Med. Hyg. 50(3): 322–8, 1994). Resolved proteins were transferred electrophoretically to IMMOBILON-P™ membrane sheets, a nitrocellulose membrane membrane sheets. Proteins were detected by staining with colloidal gold and viral antigens were identified immunologically using a non-isotopic modification of the Western blot procedure (Burnett, W. N. *Anal. Biochem.* 112: 195–203, 1981; Feighny, R. et al., 1992, supra).

Protein assay. Total protein was determined essentially as described by Bradford (*Anal. Biochem.* 72: 248, 1976), using a commercially-available kit (BioRad, Hercules, Calif.) and bovine serum albumin (BSA) or gamma globulin as a standard.

Mouse immunization and protection assays. Five to six week-old, outbred, ICR mice (Jackson Labs) were immunized with inactivated dengue virus with or without an adjuvant. Adjuvants used were Freund's complete (FCA) followed by incomplete (Difco) as a 1:1 emulsion with antigen, Hunter's Titer Max (HTM, Vaxcell) as a 1:1 emulsion with antigen, or aluminum hydroxide (alum, ALHYDROGEL™, Superfos Biosector a/s, 2%, Sergeant Chemical Co.) as a 0.1% suspension with antigen. Inoculations of 0.1 to 0.2 ml volumes were given with a 22 g needle by the subcutaneous (SQ) route in the region of the hind quadriceps. Two inoculations were given spaced 1 month apart. Blood for serological analysis was obtained 1 month after the first and 2 weeks after the second inoculation by retro-orbital puncture using sterile glass capillary pipettes.

For protection assays, three-week-old Balb/c mice were inoculated SQ in the hindquarters with inactivated dengue viruses in a 0.1% suspension with alum in PBS (0.1 ml). Mice were boosted with an equivalent dose two weeks later. At six weeks of age immunized mice were inoculated intracranially (IC) using a 26 g needle with approximately $10^5$ PFU of live, mouse-adapted dengue-2 virus (NGC strain) contained in 30–50 uL of HBSS. Challenged mice were monitored daily for morbidity and mortality for up to twenty-one days and scored according to morbidity status (N) as follows: healthy, N=0; ruffled haircoat, lethargic, N=1; partial hindlimb paralysis, N=2; complete hindlimb paralysis, wasting, N=3. For comparison among vaccine and control groups a 'mean morbidity score' was calculated as follows: The summation, from N=0 to N=3, of {N×no. of mice at status N on a given day / total no. of surviving mice on that day} total no. of days of illness.

EXAMPLE I

Dengue virus growth and purification

Following the general scheme outlined in FIG. 1, selected dengue-2 virus isolates were used to prepare several pilot lots of inactivated virus vaccine. Roller bottle cultures of FRhL-2 cells were infected with dengue-2 virus, strain 16681, and cultures of Vero-PM cells were infected with dengue-2 virus, strain S16803. After virus adsorption, the cultures were fed with maintenance medium containing 2% FBS (for FRhL-2 cells) or 0.25% HSA (for Vero-PM cells). In some experiments with Vero-PM cells, the regular maintenance medium was replaced with serum-free medium at 2 days PI.

In infected FRhL-2 cell cultures, virus reached titers of around $10^5$ to $10^6$ PFU/ml by 3–4 days PI and then remained relatively constant out to 7 days PI without the appearance of appreciable CPE. Virus was harvested from these cultures daily, from 4 to 7 days PI, by collecting the supernates and refeeding the cells. In contrast, Infected Vero-PM cells became rounded, refractile and began to detach from the monolayer beginning around 3 days PI. By 45 days PI when CPE was approximately 75%, virus titers of around $10^6$ to $10^7$ PFU/ml were obtained. Culture supermates were harvested only once, at 5 days PI.

Vero-PM culture supernates were concentrated by ultrafiltration and FRhL-2 culture supernates were concentrated by precipitation with PEG followed by differential centrifugation to pellet virus. The concentrated viruses were purified by ultracentrifugation on sucrose gradients. Fractions were collected and assayed for virus by HA or antigen spot blot assays (FIG. 2). Virus-positive fractions were pooled and passed through a 0.22 um filter to remove aggregates prior to formalin inactivation. Detailed results are shown from two virus purifications from Vero-PM cultures infected with dengue-2, S16803, and maintained either in the presence of 0.25% HSA (table 1) or without HSA (table 2). These and additional experiments, including purification of dengue-2, 16681, from FRhL-2 cell cultures, are summarized in table 3.

TABLE 1

Dengue-2 16803 grown in Vero-PM cells in the presence of 0.25% HSA (Lot WR3)

| Sample | Total Volume (ml) | TotalPFU (PFU/Cell) | % Yield | Total HAU | % Yield | Total Protein (mg) | % Yield | Spec. Act.[a] |
|---|---|---|---|---|---|---|---|---|
| Day 5 Culture Supernate[b] | 950 | $6.7 \times 10^9$ (11.2)[c] | 100 | 60,800 | 100 | 1,710 | 100 | $3.9 \times 10^6$ |
| Filtron Concentrate | 55 | $3.5 \times 10^9$ | 52 | 88,000 | 144 | 1,364 | 80 | $2.6 \times 10^6$ |
| Sucrose Gradient Pool | 50 | $4.7 \times 10^9$ | 70 | 40,000 | 65 | 70 | 4 | $6.7 \times 10^7$ |
| 0.22 $\mu$m Filtration | 50 | $2.4 \times 10^9$ | 36 | 15,000 | 25 | 23.5 | 14 | $1.0 \times 10^8$ |

[a]Specific activity (PFU/mg protein)
[b]Havested from ten 490 $cm^2$ roller bottles
[c]Based on $6 \times 10^7$ cells per roller bottle

TABLE 2

Dengue-2 16803 grown in Vero-PM cells the absence of serum protein (Lot WR 4)

| Sample | Total Volume (ml) | Total PFU(PFU/ Cell) | % Yield | Total HAU | % Yield | Total Protein (mg) | % Yield | Spec. Act.[a] |
|---|---|---|---|---|---|---|---|---|
| Day 5 Culture Supernate[b] | 960 | $1.7 \times 10^{10}$ (28.3)[c] | 100 | 61,440 | 100 | 139 | 100 | $1.2 \times 10^8$ |
| Filtron Concentrate | 75 | $1.2 \times 10^{10}$ | 71 | 120,000 | 195 | 62 | 45 | $1.9 \times 10^8$ |
| Sucrose Gradient Pool | 50 | $1.1 \times 10^{10}$ | 65 | 40,000 | 65 | 9.7 | 7 | $1.1 \times 10^9$ |
| 0.22 μm Filtration | 50 | $4.0 \times 10^9$ | 24 | 20,000 | 32 | 7.5 | 5.4 | $5.3 \times 10^8$ |

[a]Specific activity (PFU/mg protein)
[b]Havested from ten 490 cm² roller bottles
[c]Based on $6 \times 10^7$ cells per roller bottle

TABLE 3

Summary of dengue-2 virus vaccine lots

| Lot No. | Virus Strain | Cell Substrate | Total Volume (ml) | PFU Equivalents (per ml) | Protein (μg/ml) | % Yield (PFU) |
|---|---|---|---|---|---|---|
| M1 | Den-2 S16681 | FRhL-2 | 3.2 | $3.1 \times 10^8$ | 400 | ND |
| M2 | Den-2 S16681 | FRhL-2 | 9.2 | $3.2 \times 10^8$ | 430 | 9.3 |
| WR2 | Den-2 S16803 | Vero-PM | 50 | $6.8 \times 10^7$ | 550 | 11.3 |
| WR3 | Den-2 S16803 | Vero-PM | 50 | $4.8 \times 10^7$ | 470 | 36 |
| WR4 | Den-2 S16803 | Vero-PM | 50 | $8.0 \times 10^7$ | 150 | 24 |

ND, Not determined

Virus samples from sucrose gradient pools were then subjected to electrophoresis on polyacrylamide gels containing the detergent sodium dodecylsulfate (SDS-PAGE). The resolved protein bands were detected by staining with colloidal gold (FIG. 3A). Virus antigens were detected by Western blotting with mouse anti-dengue polyclonal antibody (FIG. 3B), a mixture of monoclonal antibodies reactive with E antigen (FIG. 3C), and a mixture of monoclonal antibodies reactive with prM/M and NS1 antigens (FIG. 3D). In virus purified from Vero-PM cells, E and prM/M antigens were seen, along with smaller amounts of the dimer form of NS1 (FIG. 3D). In virus purified from FRhL-2 cells, E and a triplet band of low molecular weight which reacted with polyclonal antibody but not prM/M monoclonal antibodies were the major antigens detected (data not shown).

Roller bottle cultures of Vero-PM and FRhL-2 cells, both potentially acceptable cell substrates, were used for large scale virus propagation. Although FRhL-2 cells showed less CPE and grew to a lower cell density, the overall virus yield on a per cell basis was somewhat higher than with Vero-PM cells, possibly because FRhL-2 cells were harvested several times during infection. This advantage may be offset, however, since Vero-PM cultures could be refed with serum-free medium at 2 days PI without measurable losses in virus titer. The ability to eliminate serum proteins from infected cultures should allow a potential dengue vaccine to more easily meet accepted purity standards for inactivated vaccines (Assaad, F. et al. *WHO Technical Report Series* 747: 93–103, 1987).

EXAMPLE 2

Dengue virus inactivation

Purified dengue-2 virus was then inactivated with formalin or gamma radiation. Inactivation with 0.05% formalin was carried out at 22 C. Samples were taken at regular intervals and assayed directly for infectious virus by plaque titration (FIG. 4). Samples which were negative by direct plaque assay were subjected to blind passage on C6/36 cell monolayers in order to amplify low levels of virus and then re-plaqued. It was found that 60–84 hrs was required for complete inactivation of infectivity. Inactivation with formalin under these conditions was carried out for at least 180 hrs, giving a three-fold margin of safety. The antigenicity of the virus was monitored during inactivation by testing samples with the antigen spot blot assay and polyclonal antisera. By this assay there appeared to be no detectable losses in antigenicity after exposure to 0.05% formalin for up to 208 hrs.

Alternatively, virus was inactivated by exposure to a $^{60}Co$ source. It was determined empirically that 5.5 MRads was the minimum dose required for complete inactivation (data not shown). Final inactivation was carried out with a dose of 7 MRads. At both 5.5 and 7 MRads there were some losses in the antigenicity of the virus which prevented higher doses from being tested.

Virus purification was carried out by sucrose density gradient ultracentrifugation. Virus from Vero-PM cells gave a sharp peak with a trailing shoulder which was detected by HA and which coincided with a visible band. From the position of the peak in the gradient it was assumed to represent intact virions while the shoulder may represent incomplete virions or slow-sedimenting hemagglutinin (SHA) particles (Stollar, V. *Virology* 39: 426–38, 1969). In contrast, virus grown in FRhL-2 cells gave a very broad "peak" which was detected by antigen spot blot assay (HA was not performed), but no distinct, visible band was seen in the gradients (data not shown). The broad peak may have been due to residual soluble antigens present in the concentrated virus sample which reacted in the spot blot assay. Only the leading part of this peak was pooled; therefore, recovery of infectivity was lower than that observed with virus purified from Vero-PM cultures.

The virus preparations were compared for relative purity using specific activity measurements (i.e., PFU/mg protein) and Western blot analysis. Virus purified from Vero-PM cultures without serum supplements had about the same specific activity as virus purified from FRhL-2 cultures with 2% FBS. However, the virus purified from FRhL-2 cultures was subjected to two additional differential centrifugation steps which probably accounted for its increased specific activity. When virus purified from Vero-PM cells was examined by SDS-PAGE and Western blotting, E and prM/M antigens were seen along with smaller amounts of NS1. In addition to these antigens, an antigen(s) whose identity is not known, which gave rise to a distinct low MW triplet band, was seen in virus purified from FRhL-2 cultures. Following purification, viruses were inactivated with either 0.05% formalin or gamma irradiation using a $^{60}$Co source. Although formalin is classically employed to inactivate viruses, its effect on the antigenicity and immunogenicity of purified dengue viruses has not been well studied, prompting the use of gamma irradiation as an alternative. Reactivity with dengue virus polyclonal antibody in an antigen spot blot assay was chosen as a rapid, convenient way to monitor antigenicity during inactivation. After formalin inactivation, there were generally no detectable losses in gross antigenicity, however, it was not possible to rule out limited losses of individual epitopes. After gamma irradiation, however, there were measurable losses in antigenicity even at the lowest dose required for complete inactivation of infectivity. In addition, gamma irradiation appeared to destroy the ability of virus to elicit high titers of hemagglutination-inhibiting (HI) antibody in mice (see below).

The inactivated virus preparations were then used to immunize mice. Two inoculations were required for development of high antibody titers. Neutralizing antibody titers, for example, increased six to seven-fold after a boost. Comparison of viruses inactivated by gamma-irradiation and formalin showed that although both elicited similar titers of neutralizing antibody, only formalin-inactivated virus elicited high-titered HI antibody. However, the role, if any, of HI antibody in immunity to dengue is unknown. Comparison of different adjuvants showed that Freund's was superior to all other adjuvants tested. Hunter's Titer Max (HTM), a synthetic block copolymer, performed well only at high antigen doses. Aluminum hydroxide (alum), the only adjuvant used in this study which is suitable for human use, performed almost as well as Freund's at lower antigen doses. Antibody titers obtained without an adjuvant were significantly lower than those obtained with an adjuvant.

Although there are no animals that respond to dengue infection like humans, including sub-human primates, in which infection is subclinical, manifested only by viremia, there are mouse encephalitis models (Meiklejohn, G. et al. Am. J. Trop. Med. Hyg. 1: 51–8, 1952; Schlesinger, R. W. and Frankel, J. W. Am. J. Trop. Med. Hyg. 1: 66–77, 1952) which are convenient and widely used to test dengue immunogens for protective efficacy. Two fonnalin-inactivated virus preparations, WR 3 and WR 4, were tested in Balb/c mice for their ability to protect against morbidity and mortality following intracranial challenge with live virus. Both preparations were protective; WR 4 conferred complete protection with only two 0.15 ug doses, making this preparation a good candidate for further evaluation.

EXAMPLE 3

Immunogenicity of purified, inactivated dengue-2 virus in mice

The immunogenicity of purified, inactivated dengue-2 virus preparations were then tested in mice. Adult, outbred mice were immunized with various dilutions of inactivated dengue-2 viruses with or without adjuvants. Mice received either one or two inoculations spaced one month apart. Sera obtained from immunized mice were tested for the presence of HI and neutralizing antibodies (table 4). Mice immunized with formalin-inactivated virus developed high-titered neutralizing and HI antibodies after two inoculations. Mice immunized with irradiated virus developed high-titered neutralizing but only low-titered HI antibodies. Adjuvants significantly improved the immune response of mice to inactivated viruses.

The protective efficacy of formalin-inactivated dengue-2 virus was then tested in Balb/c mice. Mice were immunized at three weeks of age with inactivated dengue-2 virus mixed with alum and boosted at five weeks of age. Age-matched controls were inoculated with PBS or a non-specific antigen in alum. The mice were challenged at six weeks of age by intracranial inoculation with mouse-neurovirulent dengue-2 virus (NGC strain) and observed daily for morbidity and mortality. Results from two separate experiments are shown in table 5. In both experiments, all vaccinated mice remained healthy after virus challenge (mean morbidity score of 0). In comparison, all mice in the control groups becme sick (mean morbidity scores of 1.70 and 1.25) beginning at six to seven days post-challenge. The mortality rates among controls were 47% ($p<0.05$) and 80% ($p<0.01$) in the two experiments.

The results presented here suggest that an inactivated dengue virus vaccine may be feasible. Relatively fast and efficient processes were developed for growing dengue-2 viruses in Vero-PM and FRhL-2 cells, concentrating and purifying them to a degree which may be suitable for human use, and inactivating them without measurable losses in antigenicity. These preparations were found to be immunogenic and protective in mice.

TABLE 4

Immune Response of Mice Vaccinated with Inactivated Dengue Virus[a]

| Vaccine lot[b] | Doses × µg/dose[c] | Adjuvant | PRNT-50%[d] | HI |
|---|---|---|---|---|
| WR2 | 2 × 55 | FCA | 16,000 | 1280 |
| WR2 | 2 × 18 | FCA | 2,500 | 160 |
| WR2 | 2 × 5.5 | FCA | 600 | 160 |
| WR2 | 2 × 1.8 | FCA | 900 | 160 |
| WR2 | 2 × 0.5 | FCA | 1,200 | 80 |
| WR3 | 1 × 47 | Alum | 160 | <10 |
| WR3 | 1 × 15.5 | Alum | 340 | <10 |
| WR3 | 2 × 47 | Alum | 800 | 40 |
| WR3 | 2 × 15.5 | Alum | 1,400 | 160 |
| WR3 | 2 × 4.7 | Alum | 350 | 80 |
| WR4 | 1 × 15 | Alum | 280 | <10 |
| WR4 | 1 × 5 | Alum | 230 | <10 |
| WR4 | 2 × 15 | Alum | 1,200 | 160 |
| WR4 | 2 × 5 | Alum | 2,500 | 320 |
| WR4 | 2 × 1.5 | Alum | 900 | 160 |
| M1(F[f]) | 2 × 12 | FCA | 4,400 | 640 |
| M1(F) | 2 × 1.2 | FCA | 4,600 | 640 |
| M1(F) | 2 × 12 | HTM | 2,800 | 640 |
| M1(F) | 2 × 1.2 | HTM | 180 | 40 |
| M1(F) | 2 × 12 | none | 720 | 320 |
| M1(F) | 2 × 1.2 | none | 170 | 80 |
| M1(G[g]) | 2 × 12 | FCA | 2,300 | 160 |
| M1(G) | 2 × 1.2 | FCA | 980 | 80 |
| M1(G) | 2 × 12 | Alum | 1,100 | 160 |
| M1(G) | 2 × 1.2 | Alum | 820 | 80 |
| M1(G) | 2 × 12 | none | 320 | 40 |
| M1(G) | 2 × 1.2 | none | 540 | 10 |

[a]Assays were performed on pooled sera from 5 mice per group.
[b]See table 3
[c]Total protein administered by SQ route in 0.1 ml
[d]Endpoint titer (reciprocal of serum dilution) giving 50% reduction of dengue-2 virus plaques
[e]Endpoint titer (reciprocal of serum dilution) giving complete hemagglutination
[f]Formalin-inactivated virus
[g]Gamma radiation-inactivated virus

TABLE 5

Protection of Vaccinated Mice Against Challenge With Live Dengue-2 Virus[a]

| Experiment | Vaccine Lot[b] | $\mu$g/dose | Mean Morbidity[c] | Survivors | p[d] |
|---|---|---|---|---|---|
| One | Control[e] | N/A | 1.70 | 8/15 | <0.05 |
| | WR3 | 15.5 | 0 | 10/10 | |
| | WR4 | 5 | 0 | 10/10 | |
| Two | Control | N/A | 1.25 | 2/10 | <0.01 |
| | WR4 | 1.5 | 0 | 10/10 | |
| | WR4 | 0.15 | 0 | 9/9 | |

[a]Mice immunized with 2 doses of vaccine, then challenged with mouse-neurovirulent dengue-2 NGC virus
[b]See table 3
[c]Calculated as described in Materials and Methods section
[d]Calculated by comparing mortality between controls and vaccinated animals using Fisher's exact test
[e]Saline or culture supernate from uninfected cells

EXAMPLE 4

Immunogenicity of purified inactivated dengue-2 virus in Rhesus monkeys

Adult Rhesus monkeys were immunized with various dilutions of purified inactivated virus (PIV) with alum. Two inoculations were given, spaced one month apart. Sera obtained one month after the first inoculation and two weeks after the second inoculation were tested for neutralizing (N) antibodies (table 6). After the first inoculation, 8 of 9 animals responded with N antibody. After the second inoculation, all animals had N antibodies (PRNT-50% mean titer of 560). There was no significant difference in N antibody titers between groups which received the highest and lowest doses of PIV.

Therefore, in vaccinated rhesus monkeys, nearly 90% of animals had measurable N antibodies one month after a single inoculation with as little as 7.5 ug of protein. Two weeks after a second inoculation, N antibody titers increased significantly to levels which, presumably, would be protective.

TABLE 5

Immune Response of Rhesus Monkeys Vaccinated with Inactivated Dengue Virus[a]

| Vaccine[b] | Animal number | Inoculation one N | Inoculation two N |
|---|---|---|---|
| WR-4, undiluted (75 $\mu$g) | 4B6 | 20 | 360 |
| | CH137 | >40 | 660 |
| | 882C | 10 | 620 |
| WR-4, 1:3 (25 $\mu$g) | 033A | >40 | 760 |
| | 891558 | >40 | 840 |
| | 68A | <10 | 30 |
| WR-4, 1:10(7.5 $\mu$g) | 3MI | 10 | 160 |
| | 547A | 20 | 1,100 |
| | 6PR | >40 | 540 |
| Saline controls | CH139 | <10 | <10 |
| | M2 | <10 | <10 |
| | E363 | <10 | <10 |

TABLE 5-continued

[a]Adult Rhesus monkeys were inoculated with the indicated doses of dengue-2 PIV in alum or with saline (control).
[b]Total protein for each inoculation is given in parentheses. Also see Table 2.

The foregoing invention has been described in some detail by way of examples for purposes of clarity and understanding. It will be obvious to those skilled in the art from a reading of the disclosure that variations in form and detail can be made without departing from the scope of the invention.

What is claimed is:

1. A method for detecting an antibody directed against a dengue virus antigen comprising:
(i) incubating a sample suspected of containing anti-dengue antibodies with purified inactivated dengue virus wherein said inactivated dengue virus is one or more purified inactivated dengue virus selected from the group consisting of dengue virus type 1 having accession no. VR-2649, dengue virus type 2 having accession no. VR-2650, dengue virus type 3 having accession no. VR-2654, and dengue virus type 4 having accession no. VR-2651 under conditions which allow the formation of an antibody-inactivated virus complex; and
(ii) detecting said antibody by detecting the antibody-inactivated virus complex.

2. A diagnostic kit for the detection of antibodies against dengue virus antigens in a sample, said kit comprising one or more purified, inactivated dengue virus selected from the group consisting of dengue virus type 1 having accession no. VR-2649, dengue virus type 2 having accession no. VR-2650, dengue virus type 3 having accession no. VR-2654, and dengue virus type 4 having accession no. VR-2651, for use in detecting said antibodies.

3. A method for detecting an antibody directed against a dengue virus antigen according to claim 1, wherein said inactivated virus is chemically inactivated.

4. The diagnostic kit according to claim 2 wherein said inactivated dengue virus is chemically inactivated.

5. The method according to claim 1 wherein said dengue virus antigen is a dengue virus type 1 antigen, and said inactivated dengue virus is dengue virus type 1 having ATCC accession no. VR-2649.

6. The method according to claim 1 wherein said dengue virus antigen is a dengue virus type 2 antigen, and said inactivated dengue virus is dengue virus type 2 having ATCC accession no. VR-2650.

7. The method according to claim 1, wherein said dengue virus antigen is a dengue virus type 3 antigen, and said inactivated dengue virus is dengue virus type 3 having ATCC accession no. VR-2654.

8. The method according to claim 1, wherein said dengue virus antigen is a dengue virus type 4 antigen, and said inactivated dengue virus is dengue virus type 4 having ATCC accession no. VR-2651.

* * * * *